(12) United States Patent
Kilambi et al.

(10) Patent No.: US 8,568,533 B2
(45) Date of Patent: Oct. 29, 2013

(54) MULTISTAGE CELLULOSE HYDROLYSIS AND QUENCH WITH OR WITHOUT ACID

(75) Inventors: Srinivas Kilambi, Duluth, GA (US); Kiran Kadam, Golden, CO (US); Cheryl A. Martin, Washington, DC (US)

(73) Assignee: Renmatix, Inc., King of Prussia, PA (US)

( * ) Notice: Subject to any disclaimer, the term of this patent is extended or adjusted under 35 U.S.C. 154(b) by 6 days.

(21) Appl. No.: 13/464,366

(22) Filed: May 4, 2012

(65) Prior Publication Data
US 2012/0285445 A1 Nov. 15, 2012

Related U.S. Application Data

(60) Provisional application No. 61/482,382, filed on May 4, 2011.

(51) Int. Cl.
C13B 20/16 (2011.01)

(52) U.S. Cl.
USPC .......................................................... 127/57

(58) Field of Classification Search
None
See application file for complete search history.

(56) References Cited

U.S. PATENT DOCUMENTS

| | | | |
|---|---|---|---|
| 2,198,785 A | 4/1940 | Mohr et al. | |
| 2,356,500 A | 8/1944 | Boinot | |
| 2,516,833 A | 8/1950 | Ant-Wuorinen | |
| 2,681,871 A | 6/1954 | Wallace | |
| 2,759,856 A | 8/1956 | Saums et al. | |
| 2,801,939 A | 8/1957 | Hignett et al. | |
| 3,212,932 A | 10/1965 | Hess et al. | |
| 3,314,797 A | 4/1967 | Hess et al. | |
| 4,201,596 A | 5/1980 | Church et al. | |
| 4,427,453 A | 1/1984 | Reitter | |
| 4,468,256 A | 8/1984 | Hinger | |
| 4,556,430 A | 12/1985 | Converse et al. | |
| 4,612,286 A | 9/1986 | Sherman et al. | |
| 4,637,835 A | 1/1987 | Nagle | |
| 4,699,124 A | 10/1987 | Nagle | |
| 5,125,977 A | 6/1992 | Grohmann et al. | |
| 5,705,369 A | 1/1998 | Torget et al. | |
| 6,022,419 A | 2/2000 | Torget et al. | |
| 6,921,820 B2 | 7/2005 | Arai et al. | |
| 8,057,639 B2 | 11/2011 | Pschorn et al. | |
| 2008/0032344 A1* | 2/2008 | Fallavollita | 435/72 |

(Continued)

FOREIGN PATENT DOCUMENTS

| | | |
|---|---|---|
| DE | 3225074 | 1/1984 |
| EP | 98490 | 1/1984 |

(Continued)

OTHER PUBLICATIONS

International Patent Application No. PCT/US2012/036583, "International Search Report and Written Opinion Received", Nov. 30, 2012, 10 pages.

(Continued)

*Primary Examiner* — Melvin C Mayes
*Assistant Examiner* — Stefanie Cohen
(74) *Attorney, Agent, or Firm* — Kilpatrick Townsend & Stockton LLP; Travis B. Gasa

(57) ABSTRACT

Methods are disclosed for increasing the yields of fermentable $C_6$ sugars from lignocellulosic biomass by using a multistage cellulose hydrolysis and quench, with or without acid.

52 Claims, 2 Drawing Sheets

(56) References Cited

U.S. PATENT DOCUMENTS

| | | | |
|---|---|---|---|
| 2009/0288788 | A1 | 11/2009 | Castor |
| 2010/0043782 | A1* | 2/2010 | Kilambi et al. .................. 127/1 |
| 2010/0069626 | A1 | 3/2010 | Kilambi |
| 2010/0170504 | A1 | 7/2010 | Zhang |
| 2010/0175690 | A1 | 7/2010 | Nagahama et al. |

FOREIGN PATENT DOCUMENTS

| | | |
|---|---|---|
| EP | 1686192 | 8/2006 |
| GB | 2145090 | 3/1985 |
| JP | 2001095594 | 4/2001 |
| JP | 2003212888 | 7/2003 |
| JP | 2006263527 | 10/2006 |
| JP | 2008011753 | 1/2008 |
| JP | 2008248202 | 10/2008 |
| KR | 2009030967 | 3/2009 |
| WO | 8301958 | 6/1983 |
| WO | 9967409 | 12/1999 |
| WO | 0061276 | 10/2000 |
| WO | 0132715 | 5/2001 |
| WO | 2007120210 | 10/2007 |
| WO | 2008050740 | 5/2008 |
| WO | 2009060126 | 5/2009 |
| WO | 2010034055 | 4/2010 |
| WO | 2011091044 | 7/2011 |

OTHER PUBLICATIONS

Adschiri et al., "Noncatalytic Conversion of Cellulose in Supercritical and Sub-Critical Water", Journal of Chemical Engineering of Japan, 1993, 26(6): 676-680.

Adschiri et al., "Cellulose hydrolysis in supercritical water to recover chemicals", Reaction Engineering for Pollution Prevention, 2000, 205-220.

Arai et al., "(Abstract) Biomass conversion in supercritical water for chemical recycle", Enerugi, Shigen, 16(2), 1995, 175-180.

Ehara et al., "A comparative study on chemical conversion of cellulose between the batch-type and flow-type in supercritical water", Cellulose, 2002, vol. 9, 301-311.

Ehara et al., "Decomposition behavior of cellulose in supercritical water, subcritical water, and their combined treatments", J. Wood Sci., vol. 51, 2005, 148-153.

Gong et al., "(Abstract) Study on hydrolysis and saccharification of microcrystalline cellulose in supercritical water", Xiandai Huagong, 30(2), 2010, 44-47.

Lee et al., "(Abstract) Hydrolysis of cellulose under subcritical and supercritical water using continuous flow system", Hwahak Konghak, 39(2), 2001, 257-263.

Luterbacher et al., "(Abstract) High-Solids Biphasic CO2-H2O Pretreatment of Lignocellulosic Biomass", Biotechnology and Bioengineering, 107(3), 2010, 451-460.

Malaluan et al., "Biomass conversion in supercritical water", Off. Proc. Comb. Conf., 6th Conf. Asia Pac. Confed. Chem. Eng., 21st Australas. Chem. Eng. Conf., vol. 1, 1993, 2091/1-214/1.

Matsunaga et al., "Super-rapid chemical conversion of sugi wood by supercritical and subcritical water treatment", Mokuzai Gakkaishi, 50(5), 2004, 325-32.

Mok et al., "(Abstract) Dilute acid hydrolysis of biopolymers in a semi-batch flow reactor at supercritical pressure", Energy from Biomass and Wastes, 13, 1990, 1329-1347.

Mosier et al., "(Abstract) Optimization of pH controlled liquid hot water pretreatment of corn stover", Bioresource Technology, 96(18), 2005, 1986-1992.

Nakata et al., "(Abstract) Bioethanol from cellulose with supercritical water treatment followed by enzymatic hydrolysis", Applied Biochemistry and Biotechnology, 129-132, 2006, 476-485.

Park et al., "(Abstract) Kinetics of cellulose decomposition under subcritical and supercritical water in continuous flow system", Korean Journal of Chemical Engineering, 19(6), 2002, 960-966.

Saka, "Supercritical fluids to biomass research", Cellulose Communications, 5(3), 1998, 129-35.

Saka et al., "Supercritical fluids to biomass research (II)", Cellulose Communications, 9(3), 2002, 137-43.

Saka et al., "Chemical conversion of biomass resources to useful chemicals and fuels by supercritical water treatment", Bridgewater AV(ed) Progress in Thermocritical Biomass Conversion. Blackwell, Oxford, 2001, 1338-1348.

Saka et al., "Chemical conversion of various celluloses to glucose and its derivatives in supercritical water", Cellulose Communications, 6(3), 1999, 177-191.

Sasaki et al., "Cellulose Hydrolysis in Sub-Critical and Supercritical Water", Journal of Supercritical Fluids, 1998, 13:261-268.

Sasaki et al., "Super-rapid enzymatic hydrolysis of cellulose with supercritical water solubilization pretreatment", Kobunshi Ronbunshu, 58(10), 2001, 527-32.

Sasaki et al., "Rapid and selective conversion of cellulose to valuable chemical intermediates using supercritical water", Proc. 6th international Symposium on Supercritical Fluids, Tome 2, 2003, 1417-1422.

Sasaki et al., "Dissolution and Hydrolysis of Cellulose in Subcritical and Supercritical Water", Industrial & Engineering Chemistry Research, 39(8), 2000, 2883-2890.

Sasaki et al., "Kinetics of cellulose conversion at 25 MPa in sub-and supercritical water", AIChE Journal, 50(1), 2004, 192-202.

Sera et al., "Development of saccharification techniques for cellulosic biomass", Hitz Giho, 68(2), 2008, 40-5.

Soederstroem et al., "(Abstract) Effect of Washing on Yield in One- and Two-Step Steam Pretreatment of Softwood for Production of Ethanol", Biotechnology Progress, 20(3), 2004, 744-749.

Srinivasan et al., "Pretreatment of Guayule Biomass Using Supercritical Carbon Dioxide-Based Method", Bioresource Technology, 101(24), 2010, 9785-9791.

Vick Roy et al., "Biomass hydrolysis with sulfur dioxide and water in the region of the critical point", Process Technology Proceedings, 3 Supercrit. Flud Technol., 1985, 397-444.

Zhao et al., "Fermentable hexose production from corn stalks and wheat straw with combined supercritical and subcritical hydrothermal technology", Bioresource Technology, 100(23), 2009, 5884-5889.

Zhao et al., "Supercritical hydrolysis of cellulose for oligosaccharide production in combined technology", Chemical Engineering Journal, Aug. 1, 2009, 150(2):411-417.

Zhao et al., "Combined supercritical and subcritical process for cellulose hydrolysis to fermentable hexoses", Environmental Science & Technology, 43(5), 2009, 1565-1570.

Zhao et al., "Supercritical pretreatment and hydrolysis of cellulose", Huaxue Xuebao, 66(20), 2008, 2295-2301.

* cited by examiner

US 8,568,533 B2

MULTISTAGE CELLULOSE HYDROLYSIS AND QUENCH WITH OR WITHOUT ACID

CROSS REFERENCE TO RELATED APPLICATIONS

This application claims the benefit of U.S. Application No. 61/482,382, filed May 4, 2011, the entire disclosure of which is incorporated herein by reference.

FIELD OF THE INVENTION

The present invention generally relates to methods of increasing the yields of fermentable $C_6$ sugars from lignocellulosic biomass. More particularly, it relates to methods of increasing the yields of fermentable $C_6$ sugars from lignocellulosic biomass by using a multistage cellulose hydrolysis and quench, with or without acid.

BACKGROUND OF THE INVENTION

There exist methods for converting lignocellulosic biomass into fermentable $C_5$ and $C_6$ sugars. Several of these methods first produce oligomers of the $C_5$ and $C_6$ sugars, which are then hydrolyzed to form fermentable streams of monomers of $C_5$ and $C_6$ sugars. Problems exist with current methods, including, inter alia, control issues due to the very short residence times in the reactor leading to unwanted degradation products, such as acids, that inhibit fermentation. It would, therefore, be beneficial to develop methods that would be scalable, that maximize monomer formation, and that minimize the formation of degradation products. The methods and compositions of the present invention are directed toward these, as well as other, important ends.

SUMMARY OF THE INVENTION

The present invention provides, inter alia, process improvements that enhance reaction control by quickly getting reactants to the appropriate reaction temperature and then quickly reducing the temperature to arrest reaction to prevent the formation of undesired degradation products.

In one embodiment, the invention is directed to methods of increasing the level of $C_6$ monosaccharides and $C_6$ oligosaccharides produced from lignocellulosic biomass, comprising:
  providing lignocellulosic biomass, comprising:
    a first solid fraction comprising:
      cellulose; and
      lignin; and
    a first liquid fraction;
  optionally, separating said first solid fraction and said first liquid fraction;
  mixing said first solid fraction with water to form a slurry;
  pre-heating said slurry to a temperature of about 210° C. to about 240° C. at a pressure of about 225 bar to about 250 bar;
  contacting said slurry with a second reaction fluid to form a second reaction mixture comprising:
    a second solid fraction comprising:
      lignin; and
    a second liquid fraction comprising:
      a soluble $C_6$ saccharide selected from the group consisting of $C_6$ monosaccharides, $C_6$ oligosaccharides, and mixtures thereof;
  wherein said second reaction fluid comprises hot compressed water and, optionally, carbon dioxide;
  wherein said second reaction fluid is at a temperature of at least about 373° C. under a pressure sufficient to maintain said second reaction fluid in supercritical form; and
  reducing the temperature of said slurry to a temperature less than about 140° C.; and
  optionally, hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof.

In another embodiment, the invention is directed to methods of controlling the rate of cellulose hydrolysis, comprising:
  providing lignocellulosic biomass, comprising:
    a first solid fraction comprising:
      cellulose; and
      lignin; and
    a first liquid fraction;
  optionally, separating said first solid fraction and said first liquid fraction;
  mixing said first solid fraction with water to form a slurry;
  pre-heating said slurry to a temperature of about 210° C. to about 240° C. at a pressure of about 225 bar to about 250 bar;
  contacting said slurry with a second reaction fluid to form a second reaction mixture:
    a second solid fraction comprising:
      lignin; and
    a second liquid fraction comprising:
      a soluble $C_6$ saccharide selected from the group consisting of $C_6$ monosaccharides, $C_6$ oligosaccharides, and mixtures thereof;
  wherein said second reaction fluid comprises hot compressed water and, optionally, carbon dioxide;
  wherein said second reaction fluid is at a temperature of at least about 373° C., preferably at least about 380° C., under a pressure sufficient to maintain said second reaction fluid in supercritical form;
  reducing the temperature of said slurry to a temperature less than about 140° C.; and
  optionally, hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof.

In yet other embodiments, the invention is directed to methods of reducing the rate of glucose degradation, comprising:
  providing lignocellulosic biomass, comprising:
    a first solid fraction comprising:
      cellulose; and
      lignin; and
    a first liquid fraction;
  optionally, separating said first solid fraction and said first liquid fraction;
  mixing said first solid fraction with water to form a slurry;
  pre-heating said slurry to a temperature of about 210° C. to about 240° C. at a pressure of about 225 bar to about 250 bar for a residence time of about 20 seconds to about 45 seconds;
  contacting said slurry with a second reaction fluid to form a second reaction mixture comprising:
    a second solid fraction comprising:
      lignin; and a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C., preferably at least about 380° C., under a pressure sufficient to maintain said second reaction fluid in supercritical form;
reducing the temperature of said slurry to a temperature less than about 140° C.; and
optionally, hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof.

In other embodiments, the invention is directed to methods, comprising:
providing lignocellulosic biomass, comprising:
a first solid fraction comprising:
cellulose; and
lignin; and
a first liquid fraction;
optionally, separating said first solid fraction and said first liquid fraction;
mixing said first solid fraction with water to form a slurry;
pre-heating said slurry to a temperature of about 210° C. to about 240° C. at a pressure of about 225 bar to about 250 bar;
contacting said slurry with a second reaction fluid to form a second reaction mixture comprising:
a second solid fraction comprising:
lignin; and
a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C., preferably at least about 380° C., under a pressure sufficient to maintain said second reaction fluid in supercritical form;
reducing the temperature of said slurry to a temperature less than about 140° C.; and
hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof; and
converting by fermentation, catalysis, or a combination thereof said $C_6$ saccharides to a fermentation product, a catalysis product, or a mixture thereof.

In further embodiments, the invention is directed to compositions, comprising:
glucose;
water;
glyceraldehyde; and
glycolic acid;
wherein said glyceraldehyde is present at a level of less than about 13.0% glyceraldehyde, by weight, based on the total weight of the composition;
wherein said glycolic acid is present at a level of less than about 2.0% glycolic acid, by weight, based on the total weight of the composition; and
wherein said glucose is produced from said lignocellulosic biomass using supercritical or near critical fluids.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
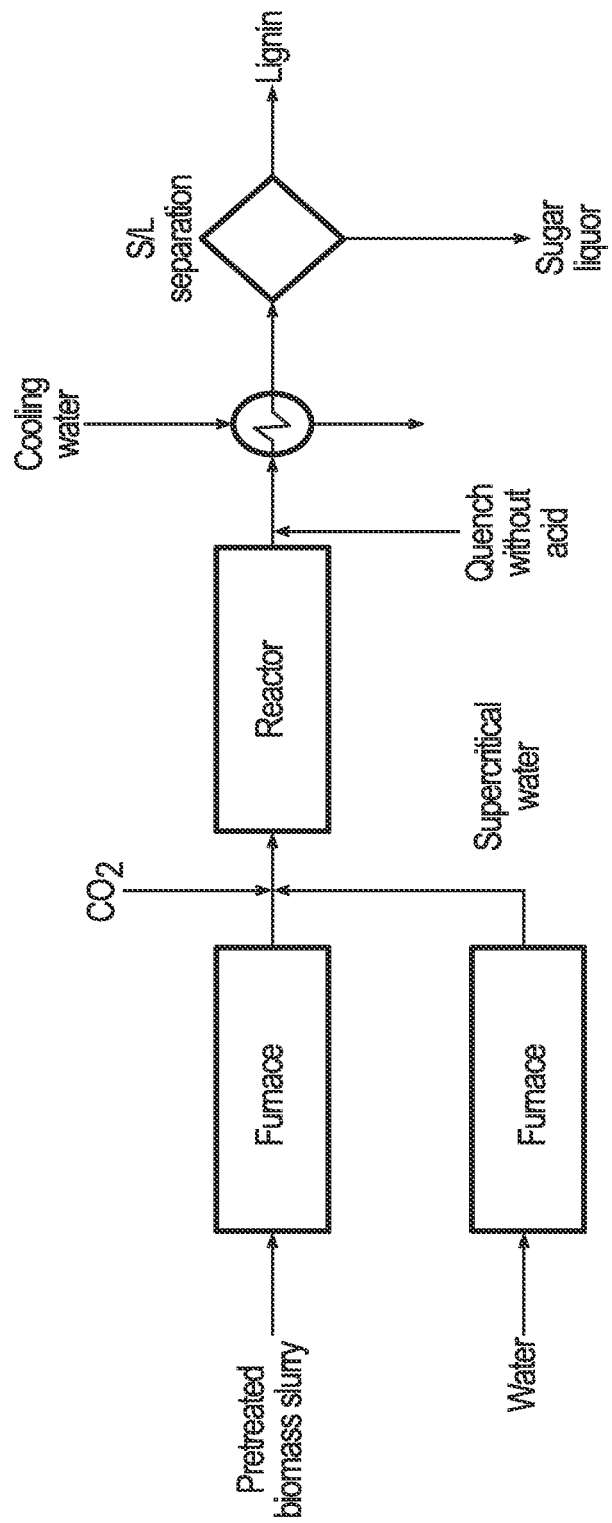
FIG. 1 is a schematic diagram for the three stage cellulose hydrolysis process with quench without acid in one embodiment of the invention.

As employed above and throughout the disclosure, the following terms, unless otherwise indicated, shall be understood to have the following meanings.

As used herein, the singular forms "a," "an," and "the" include the plural reference unless the context clearly indicates otherwise.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. Above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is used interchangeably herein for water that is at or above its critical state, or defined herein as near-critical or sub-critical, or any other temperature above about 50° C. (preferably, at least about 100° C.) but less than subcritical and at pressures such that water is in a liquid state As used herein, a fluid which is "supercritical" (e.g. supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g. water and ethanol, water and $CO_2$, etc). Thus, for example, "a mixture of sub-critical water and supercritical carbon dioxide" indicates a mixture of water and carbon dioxide at a temperature and pressure above that of the critical point for carbon dioxide but below the critical point for water, regardless of whether the supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, "continuous" indicates a process which is uninterrupted for its duration, or interrupted, paused or suspended only momentarily relative to the duration of the process. Treatment of biomass is "continuous" when biomass is fed into the apparatus without interruption or without a substantial interruption, or processing of said biomass is not done in a batch process.

As used herein, "resides" indicates the length of time which a given portion or bolus of material is within a reaction zone or reactor vessel. The "residence time," as used herein, including the examples and data, are reported at ambient conditions and are not necessarily actual time elapsed.

As used herein, the term "substantial free of" refers to a composition having less than about 1% by weight, preferably less than about 0.5% by weight, and more preferably less than about 0.1% by weight, based on the total weight of the composition, of the stated material.

As used herein, "$C_1$-$C_5$ alcohol" indicates an alcohol comprising 1 to 5 carbon atoms. Examples of $C_1$-$C_5$ alcohols include, but are not limited to, methanol, ethanol, n-propanol, isopropanol, n-butanol, s-butanol, t-butanol, i-butanol, n-pentanol, 2-pentanol, 3-pentanol, 2-methyl-1-butanol, 2-methyl-2-butanol, 3-methyl-1-butanol, 3-methyl-2-butanol, and 2,2-dimethyl-1-propanol. Mixtures of one or more of these alcohols may be used.

As used herein, "lignocellulosic biomass or a component part thereof" refers to plant biomass containing cellulose, hemicellulose, and lignin from a variety of sources, including, without limitation (1) agricultural residues (including corn stover and sugarcane bagasse), (2) dedicated energy crops, (3) wood residues (including sawmill and paper mill discards), and (4) municipal waste, and their constituent parts including without limitation, lignocellulose biomass itself, lignin, $C_6$ saccharides (including cellulose, cellobiose, $C_6$ oligosaccharides, $C_6$ monosaccharides, and $C_5$ saccharides (including hemicellulose, $C_5$ oligosaccharides, and $C_5$ monosaccharides).

As used herein, "slurry" refers to a suspension of any viscosity of solid particles in a liquid.

Accordingly, in one embodiment, the invention is directed to methods of increasing the level of $C_6$ monosaccharides and $C_6$ oligosaccharides produced from lignocellulosic biomass, comprising:
  providing lignocellulosic biomass, comprising:
    a first solid fraction comprising:
      cellulose; and
      lignin; and
    a first liquid fraction;
  optionally, separating said first solid fraction and said first liquid fraction;
  mixing said first solid fraction with water to form a slurry;
  pre-heating said slurry to a temperature of about 210° C. to about 240° C. at a pressure of about 225 bar to about 250 bar (for a residence time of about 20 seconds to about 45 seconds in certain embodiments);
  contacting said slurry with a second reaction fluid to form a second reaction mixture comprising:
    a second solid fraction comprising:
      lignin; and
    a second liquid fraction comprising:
      a soluble $C_6$ saccharide selected from the group consisting of $C_6$ monosaccharides, $C_6$ oligosaccharides, and mixtures thereof;
  wherein said second reaction fluid comprises hot compressed water and, optionally, carbon dioxide;
  wherein said second reaction fluid is at a temperature of at least about 373° C., preferably at least about 380° C., under a pressure sufficient to maintain said second reaction fluid in supercritical form;
  reducing the temperature of said slurry to a temperature less than about 140° C., preferably, less than about 100° C.; and
  optionally, hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof.

In another embodiment, the invention is directed to methods of controlling the rate of cellulose hydrolysis, comprising:
  providing lignocellulosic biomass, comprising:
    a first solid fraction comprising:
      cellulose; and
      lignin; and
    a first liquid fraction;
  optionally, separating said first solid fraction and said first liquid fraction;
  mixing said first solid fraction with water to form a slurry;
  pre-heating said slurry to a temperature of about 210° C. to about 240° C. at a pressure of about 225 bar to about 250 bar (for a residence time of about 20 seconds to about 45 seconds in certain embodiments);

contacting said slurry with a second reaction fluid to form
a second reaction mixture comprising:
a second solid fraction comprising:
lignin; and
a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C., preferably at least about 380° C., under a pressure sufficient to maintain said second reaction fluid in supercritical form;
reducing the temperature of said slurry to a temperature less than about 140° C., preferably, less than about 100° C.; and
optionally, hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof.

In yet other embodiments, the invention is directed to methods of reducing the rate of glucose degradation, comprising:
providing lignocellulosic biomass, comprising:
a first solid fraction comprising:
cellulose; and
lignin; and
a first liquid fraction;
optionally, separating said first solid fraction and said first liquid fraction;
mixing said first solid fraction with water to form a slurry;
pre-heating said slurry to a temperature of about 210° C. to about 240° C. at a pressure of about 225 bar to about 250 bar (for a residence time of about 20 seconds to about 45 seconds in certain embodiments);
contacting said slurry with a second reaction fluid to form a second reaction mixture comprising:
a second solid fraction comprising:
lignin; and
a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C., preferably at least about 380° C., under a pressure sufficient to maintain said second reaction fluid in supercritical form;
reducing the temperature of said slurry to a temperature less than about 140° C., preferably less than about 100° C.; and
optionally, hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof.

In other embodiments, the invention is directed to methods, comprising:
providing lignocellulosic biomass, comprising:
a first solid fraction comprising:
cellulose; and
lignin; and
a first liquid fraction;
optionally, separating said first solid fraction and said first liquid fraction;
mixing said first solid fraction with water to form a slurry;
pre-heating said slurry to a temperature of about 210° C. to about 240° C. at a pressure of about 225 bar to about 250 bar;
contacting said slurry with a second reaction fluid to form a second reaction mixture comprising:
a second solid fraction comprising:
lignin; and
a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C., preferably at least about 380° C., under a pressure sufficient to maintain said second reaction fluid in supercritical form;
reducing the temperature of said slurry to a temperature less than about 140° C.;
hydrolyzing said second liquid fraction to form a composition comprising at least one $C_6$ saccharide selected from the group consisting of $C_6$ oligosaccharide having lower mer units (relative to the $C_6$ oligosaccharides in said second liquid fraction), glucose, galactose, mannose, fructose, and mixtures thereof; and
converting by fermentation, catalysis, or a combination thereof said $C_6$ saccharides to a fermentation product, a catalysis product, or a mixture thereof.

Such products include, for example, ethanol and butanol, and mixtures thereof.

The methods of the invention are preferably run continuously, although they may be run as batch or semi-batch processes.

The methods of the invention may be carried out in any suitable reactor, including, but not limited to, a tubular reactor, a digester (vertical, horizontal, or inclined), or the like. Suitable digesters include the digester system described in U.S. Pat. No. 8,057,639, which include a digester and a steam explosion unit, the entire disclosure of which is incorporated by reference.

In certain embodiments, the fractionated lignocellulosic biomass is prepared by contacting said lignocellulosic biomass with a first reaction fluid comprising hot compressed water and, optionally, carbon dioxide; wherein said first reaction fluid further comprises acid, when said lignocellulosic biomass comprises softwood; and wherein said first reaction fluid is at a temperature of at least about 100° C. under a pressure sufficient to maintain said first reaction fluid in liquid form. In certain embodiments, the acid is added as an aqueous acid, is generated by contacting the first reaction fluid with a gaseous compound that forms acid in situ; and/or is generated by contacting the first reaction fluid with a solid acid catalyst. The acid may be an inorganic acid or an organic acid, or an acid formed in situ. Inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. In certain embodiments, the acid is preferably sulfuric acid, hydrochloric acid, phosphoric acid, nitric acid, or a combination thereof. Gaseous compounds that form acid in situ include, but are not limited to, $SO_2$, $CO_2$, $NO_2$, HX (where X is Cl, Br, F, or I), or a combination thereof. Suitable solid acids include, but are not limited to, zeolites, anionic exchange resins, and combinations thereof.

In certain embodiments, the step of reducing the temperature of said reaction mixture comprises contacting said reaction mixture with a composition comprising water. In certain embodiments, the composition further comprises at least one $C_1$-$C_5$ alcohol, preferably ethanol, butanol, and mixtures thereof. In certain embodiments, the $C_1$-$C_5$ alcohol(s) is present at a level of less than about 50%, based on the total weight of the composition.

In certain embodiments, the step of reducing the temperature of said reaction mixture comprises contacting said reaction mixture with a composition comprising water and acid (added separately or formed in situ), wherein said acid is present at a level less than about 1%, by weight, based on the total weight of said composition, preferably less than about 0.5%, by weight, more preferably less than about 0.3%, by weight, based on the total weight of said composition. In certain embodiments, the composition further comprises at least one $C_1$-$C_5$ alcohol, preferably acetone, ethanol, butanol, and mixtures thereof. In certain embodiments, the $C_1$-$C_5$ alcohol(s) is present at a level of less than about 50%, based on the total weight of the composition. The acid may be an inorganic acid or an organic acid. Inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. In certain embodiments, the acid is preferably sulfuric acid, hydrochloric acid, phosphoric acid, nitric acid, or a combination thereof. Gaseous compounds that form acid in situ include, but are not limited to, $SO_2$, $CO_2$, $NO_2$, HX (where X is Cl, Br, F, or I), or a combination thereof.

In certain embodiments, the slurry is preheated to a temperature of about 245° C. to about 255° C. at a pressure of about 200 bar to about 260 bar for a residence time of about 5 seconds to about one minute.

In certain embodiments, the second reaction mixture has a temperature of about 358° C. to about 380° C. at a pressure of about 200 bar to about 260 bar.

In certain embodiments, the slurry is contacted with said second reaction fluid for less than about 5 seconds, preferably less than about 2 seconds.

In certain embodiments, the reaction mixture is cooled to a temperature of about 260° C. to about 280° C. at a pressure of about 200 bar to about 260 bar.

In certain embodiments, the second liquid fraction consisting of $C_6$ monosaccharides, $C_6$ oligosaccharides, and mixtures thereof is hydrolyzed to form a $C_6$ monosaccharide selected from the group consisting of glucose, galactose, mannose, fructose, and mixtures thereof. Suitable techniques for carrying out the hydrolysis include enzymatic techniques (including using immobilized enzymes); addition of an aqueous acid; contact with a gaseous compound that forms acid in situ; and/or contact with a solid acid catalyst.

In certain embodiments, the hydrolysis step comprises adding to the second liquid fraction at least one aqueous acid selected from the group consisting of an organic acid, an inorganic acid, and mixtures thereof. Suitable inorganic acid include, but are not limited to: sulfuric acid, sulfonic acid, phosphoric acid, phosphonic acid, nitric acid, nitrous acid, hydrochloric acid, hydrofluoric acid, hydrobromic acid, hydroiodic acid. Suitable organic acids include, but are not limited to, aliphatic carboxylic acids (such as acetic acid and formic acid), aromatic carboxylic acids (such as benzoic acid and salicylic acid), dicarboxylic acids (such as oxalic acid, phthalic acid, sebacic acid, and adipic acid), aliphatic fatty acids (such as oleic acid, palmitic acid, and stearic acid), aromatic fatty acids (such as phenylstearic acid), and amino acids. In certain embodiments, the acid is preferably sulfuric acid, hydrochloric acid, phosphoric acid, nitric acid, or a combination thereof. Sulfuric acid is especially preferred. In certain embodiments, the acid is present at a level of about 0.05%, by weight, to about 2.0%, by weight, based on the total weight of the fraction to which the acid is added (either fractionated lignocellulosic biomass or first liquid fraction). In certain other embodiments, the amount of acid may be present in an amount from about 0.07% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In certain other embodiments, the hydrolysis step comprises contacting said second liquid fraction with a gaseous compound that forms acid in situ. Gaseous compounds that form acid in situ include, but are not limited to, $SO_2$, $CO_2$, $NO_2$, HX (where X is Cl, Br, F, or I), or a combination thereof. In certain embodiments, the acid is present at a level of about 0.05%, by weight, to about 2.0%, by weight, based on the weight of the liquid fraction. In certain other embodiments, the amount of acid may be present in an amount from about 0.07% to about 2%, about 0.1% to about 1.5%, about 0.1% to about 1%, about 0.1% to about 0.5%, about 0.1% to about 0.4%, about 0.1% to about 0.3%, about 0.1% to about 0.2%, about 0.5% to about 2%, about 0.5% to about 1.5%, about 0.5% to about 1%, less than about 2%, less than about 1.5%, less than about 1%, less than about 0.5%, less than about 0.4%, less than about 0.3%, less than about 0.2%, or less than about 0.1%.

In yet other embodiments, the hydrolysis step comprises contacting said second liquid fraction with a solid acid catalyst. Suitable solid acid catalysts include, but are not limited to, zeolites, anionic exchange resins, and combinations thereof.

In certain embodiments, the $C_6$ monosaccharides (glucose, galactose, mannose, fructose, and mixtures thereof) are fermented to ethanol, butanol, other alcohols, and mixtures thereof, using techniques known to those skilled in the art, including, but not limited to, yeast fermentations using *Saccharomyces cerevisiae* and *Clostridium* sp. In certain preferred embodiments, an oligomer fermentor is able to uptake oligomers directly (generally up to a maximum size, for example, of 6 mer units, for *Clostridium thermocellum*).

In certain embodiments, the yield of said glucose is at least about 63%, preferably at least about 65%, of theoretical yield.

In certain embodiments, the yield of $C_6$ monosaccharide is at least 60% of theoretical yield, preferably, at least 65% of theoretical yield.

In certain embodiments, the invention is directed to the products produced by the methods of the invention.

In further embodiments, the invention is directed to compositions, comprising:
glucose;
water;
glyceraldehyde; and
glycolic acid;
wherein said glyceraldehyde is present at a level of less than about 13.0% glyceraldehyde, by weight, based on the total weight of the composition;
wherein said glycolic acid is present at a level of less than about 2.0% glycolic acid, by weight, based on the total weight of the composition; and
wherein said glucose is produced from said lignocellulosic biomass using supercritical or near critical fluids.

Glyceraldehyde may be easily hydrogenated to mono-ethylene glycol (MEG), using Raney nickel catalyst, for example. In addition, glycolic acid, glycerolaldehyde, lactic acid, and acetic acid are generated, which may be isolated using, for example, liquid-liquid extraction.

The products produced by the methods of the invention may be utilized in a wide variety of applications, where $C_6$ sugars are conventionally utilized, including, but not limited to, the production of various chemicals and fuels using fermentative, enzymatic, catalytic, and non-catalytic (e.g., thermal decomposition) processes. Such processes are useful for preparing feedstocks for the preparation of the following non-exhaustive list:

fuels (such as gasoline, jet fuel, butanol, and the like);
chemicals (such as acetic acid, acetic anhydride, acetone, acrylic acid, adipic acid, benzene, ethanol, ethylene, ethylene glycol, ethylene oxide, methanol, polypropylene, terephthalic acid, toluene, xylene, 1,3-propanediol, 1,4-butanediol, and the like);
pharmaceuticals and foods (such as acetoin, alanine, arabitol, ascorbic acid, aspartic acid, citric acid, coumaric acid, fumaric acid, glycerol, glycine, kojic acid, lactic acid, lysine, malonic acid, proline, propionic acid, serine, sorbitol, succinic acid, threonine, xylitol, sugar acids (glucaric acid, gluconic acid, xylonic acids), and the like);
specialty chemicals (such as acontic acid, glutamic acid, malic acid, oxalic acid, and the like);
textile applications (such as formic acid and the like); and industrial intermediates (acetaldehyde, 3-hydroxypropionic acid, 2,5-furan dicarboxylic acid, furfural, glutaric acid, itaconic acid, levulinic acid, and the like).

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Three-Stage Cellulose Hydrolysis and Quench without Acid

Pre-Heat Stage

Fractionated lignocellulosic solids are mixed with water to form a slurry (4% w/w). This feed generally has a pH of about 4.2. At a pressure of 230 bar+/−30 bar, the feed is ramped up to a temperature of about 250° C.+/−5° C. and this temperature is maintained for a short residence time (about 20 seconds).

Cellulose Hydrolysis Stage

At a pressure of 230 bar+/−30 bar, preheated slurry from the pre-heat stage is then impinged (contacted) with supercritical water to reach a reaction temperature of 368° C.+/−10° C. (1:1 ratio with respect to slurry) so that the slurry temperature is immediately raised to the reaction temperature and maintained for a very short residence time (about 2 seconds according to ambient conditions).

Quench

The preheated and hydrolyzed slurry from the cellulose hydrolysis stage is then quenched with cool water to reduce the temperature by about 30° C. before sending it to the heat exchanger. The quench retards further reaction, including further hydrolysis and further degradation of monomer to unwanted degradation products, such as glycolic acid and glycolaldehyde.

Acid Post Hydrolysis

Glucose oligomer obtained from above process was quantified by conversion to monomer through acid post hydrolysis. After cooling to ambient temperature (~25° C.), slurry sample was filtered by vacuum filter and the pH of the liquid obtained was measured. Ten milliliters of the liquid sample was transferred into pressure bottle and based on sample pH, 72% w/w sulfuric acid was added to bring the acid concentration of each sample to 4%. The pressure bottles were kept well sealed and kept in the autoclave at 121° C. for 1 hour. After completion of the autoclave cycle, hydrolyzates were slowly cooled back to near room temperature before removing the seals. Calcium carbonate was slowly added to neutralize each sample to pH 5-6. Sugar recovery factor of about 0.95 for glucose was determined by sugar recovery series (SRS) subjected to the same conditions. The measured glucose monomer concentrations after post hydrolysis was then divided by sugar recovery factors to correct for sugar degradation.

A schematic for the three stage cellulose hydrolysis process with quench without acid (either as acid addition or acid formed in situ) is shown in FIG. 1.

A one-hour continuous run was conducted. Five samples were collected at similar conditions. All the liquor was collected in one container. The results are shown in the table below:

| Sample | Starting T (° C.) | T window +/− | P (bar) | P window +/− | Glucose yield (%) | Glycolaldehyde (%) |
|---|---|---|---|---|---|---|
| 1 | 367 | 6 | 228 | 21 | 65 | 12 |
| 2 | 367 | 2 | 225 | 7 | 68 | 12 |
| 3 | 365 | 2 | 219 | 2 | 66 | 11 |
| 4 | 370 | 4 | 235 | 10 | 63 | 12 |
| 5 | 373 | 7 | 230 | 19 | 57 | 16 |
| Container collected from 1 hour run | 368 | 11 | 230 | 34 | 62 | 11 |
| Average | 368 | | 228 | | 64 | 12 |

Example 2

Three-Stage Cellulose Hydrolysis and Quench with Acid

Pre-Heat Stage

Pretreated lignocellulosic solids are mixed with water to form a slurry (4% w/w). This feed generally has a pH of about 4.2. At a pressure of 230 bar+/−30 bar, the feed is ramped up to a temperature of about 250° C.+/−5° C. and this temperature is maintained for a short residence time (about 20 seconds).

Cellulose Hydrolysis Stage

At a pressure of 230 bar+/−30 bar, preheated slurry from the pre-heat stage is then impinged with supercritical water to reach a reaction temperature of 375° C.+/−5° C. (1:1 ratio with respect to slurry) so that the slurry temperature is immediately raised to the reaction temperature and maintained for a very short residence time (about 2 seconds according to ambient conditions).

Quench Stage

The preheated and hydrolyzed slurry from the cellulose hydrolysis stage is then quenched with a dilute acid stream, such as dilute sulfuric acid, at 0.2% w/w of slurry to reduce the temperature to about 270° C.+/−10° C. at a pressure of 230 bar+/−30 bar for a very short residence time (about 2 seconds according to ambient conditions), before sending it to the heat exchanger. The quench retards further reaction, including further hydrolysis and further degradation of monomer to unwanted degradation products, such as glycolic acid and glyceraldehyde. The presence of the acid converts any remaining $C_6$ oligosaccharides to smaller $C_6$ oligomers and monomer.

Acid Post Hydrolysis

Glucose oligomer obtained from above process was quantified by conversion to monomer through acid post hydrolysis. After cooling to ambient temperature (~25° C.), slurry sample was filtered by vacuum filter and the pH of the liquid obtained was measured. Ten milliliters of the liquid sample was transferred into pressure bottle and based on sample pH, 72% w/w sulfuric acid was added to bring the acid concentration of each sample to 4%. The pressure bottles were kept well sealed and kept in the autoclave at 121° C. for 1 hour. After completion of the autoclave cycle, hydrolyzates were slowly cooled back to near room temperature before removing the seals. Calcium carbonate was slowly added to neutralize each sample to pH 5-6. Sugar recovery factor of about 0.95 for glucose was determined by sugar recovery series (SRS) subjected to the same conditions. The measured glucose monomer concentrations after post hydrolysis was then divided by sugar recovery factors to correct for sugar degradation.

Figure 2:
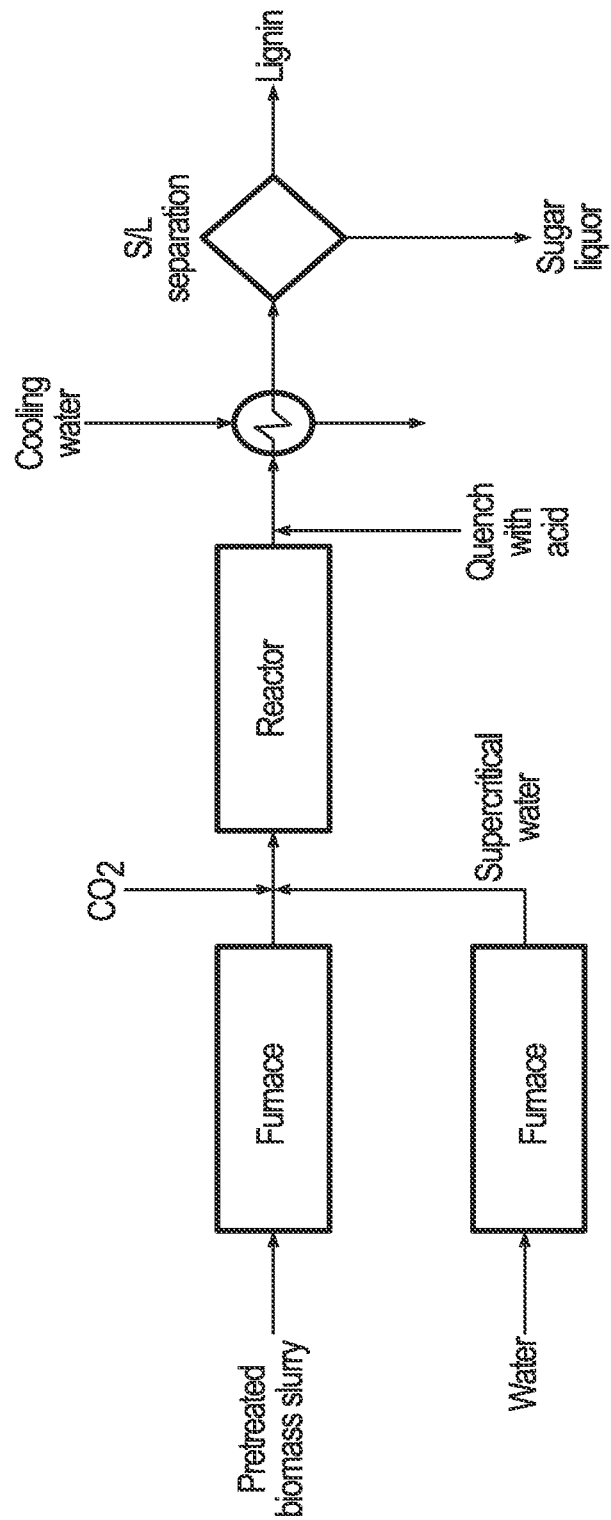
FIG. 2 is a schematic diagram for the three stage cellulose hydrolysis process with acid quench in one embodiment of the invention.

A schematic for the three stage cellulose hydrolysis process with acid quench is shown in FIG. 2.

A continuous run was conducted. Four samples were collected at similar conditions. The results are shown in the table below:

| Sample | Glucose yield (%) | Glycolaldehyde (%) | Glycolic acid + Glyceraldehyde yield (%) |
|---|---|---|---|
| 1 | 69.4 | 6.3 | 1.3 |
| 2 | 68.5 | 7.5 | 1.2 |
| 3 | 68.0 | 7.5 | 1.4 |
| 4 | 63.7 | 12.2 | 1.6 |
| Average | 67.4 | 8.375 | 1.4 |
| Standard Deviation | 2.5 | 2.6 | 0.2 |

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as molecular weight, or chemical properties, such as chemical formulae, all combinations, and subcombinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of increasing the level of $C_6$ monosaccharides and $C_6$ oligosaccharides produced from lignocellulosic biomass, comprising:
   providing lignocellulosic biomass, comprising:
      a first solid fraction comprising:
         cellulose; and
         lignin; and
      a first liquid fraction;
   optionally, separating said first solid fraction and said first liquid fraction;
   mixing said first solid fraction with water to form a slurry;
   pre-heating said slurry to a temperature of about 210° C. to about 240° C. at a pressure of about 225 bar to about 250 bar;
   contacting said slurry with a second reaction fluid to form a second reaction mixture comprising:
      a second solid fraction comprising:
         lignin; and
      a second liquid fraction comprising:
         a soluble $C_6$ saccharide selected from the group consisting of $C_6$ monosaccharides, $C_6$ oligosaccharides, and mixtures thereof;
   wherein said second reaction fluid comprises hot compressed water and, optionally, carbon dioxide;
   wherein said second reaction fluid is at a temperature of at least about 373° C. under a pressure sufficient to maintain said second reaction fluid in supercritical form; and
   reducing the temperature of said second reaction mixture to a temperature less than about 140° C.; and
   optionally, hydrolyzing said second liquid fraction to form a composition comprising at least one $C_6$ saccharide selected from the group consisting of $C_6$ oligosaccharide having lower mer units, glucose, galactose, mannose, fructose, and mixtures thereof.

2. A method of claim 1, further comprising:
   preheating said slurry to a temperature of about 245° C. to about 255° C. at a pressure of about 200 bar to about 260 bar for a residence time of about 5 seconds to about one minute.

3. A method of claim 1,
   wherein said second reaction mixture has a temperature of about 358° C. to about 380° C. at a pressure of about 200 bar to about 260 bar.

4. A method of claim 1,
   wherein said slurry is contacted with said second reaction fluid for less than about 5 seconds.

5. A method of claim 1,
wherein, prior to said reducing the temperature step, said second reaction mixture is cooled to a temperature of about 260° C. to about 280° C. at a pressure of about 200 bar to about 260 bar.

6. A method of claim 1, further comprising:
fractionating said lignocellulosic biomass prior to said providing step;
wherein said step of fractionating comprises contacting said lignocellulosic biomass with a first reaction fluid comprising hot compressed water and, optionally, carbon dioxide;
wherein said first reaction fluid further comprises acid, when said lignocellulosic biomass comprises softwood; and
wherein said first reaction fluid is at a temperature of at least about 100° C. under a pressure sufficient to maintain said first reaction fluid in liquid form.

7. A method of claim 1,
wherein said method is continuous.

8. A method of claim 1,
wherein said reducing the temperature of said second reaction mixture comprises contacting said second reaction mixture with a composition comprising water.

9. A method of claim 8,
wherein said composition further comprises at least one $C_1$-$C_5$ alcohol.

10. A method of claim 1,
wherein said reducing the temperature of said second reaction mixture comprises contacting said second reaction mixture with a composition comprising water and acid, wherein said acid is present at a level less than about 1%, by weight, based on the total weight of said composition.

11. A method of claim 10,
wherein said composition further comprises at least one $C_1$-$C_5$ alcohol.

12. A method of claim 1,
wherein said hydrolyzing said second liquid fraction is carried out enzymatically.

13. A method of claim 1,
wherein said hydrolyzing said second liquid fraction is carried out with immobilized enzyme.

14. A method of claim 1,
wherein said hydrolyzing said second liquid fraction comprises addition of at least one aqueous acid.

15. A method of claim 1,
wherein said hydrolyzing said second liquid fraction comprises contact with a gaseous compound that forms acid in situ.

16. A method of claim 1,
wherein said hydrolyzing said second liquid fraction comprises contact with at least one solid acid catalyst.

17. A method of claim 1,
wherein the yield of said glucose is at least about 63% of theoretical yield.

18. A method of controlling the rate of cellulose hydrolysis, comprising:
providing lignocellulosic biomass, comprising:
a first solid fraction comprising:
cellulose; and
lignin; and
a first liquid fraction;
optionally, separating said first solid fraction and said first liquid fraction;
mixing said first solid fraction with water to form a slurry;
pre-heating said slurry to a temperature of about 210° C. to about 240° C. at a pressure of about 225 bar to about 250 bar;
contacting said slurry with a second reaction fluid to form a second reaction mixture comprising:
a second solid fraction comprising:
lignin; and
a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C. under a pressure sufficient to maintain said second reaction fluid in supercritical form; and
reducing the temperature of said second reaction mixture to a temperature less than about 140° C.; and
optionally, hydrolyzing said second liquid fraction to form a composition comprising at least one $C_6$ saccharide selected from the group consisting of $C_6$ oligosaccharide having lower mer units, glucose, galactose, mannose, fructose, and mixtures thereof.

19. A method of claim 18, further comprising:
preheating said slurry to a temperature of about 245° C. to about 255° C. at a pressure of about 200 bar to about 260 bar for a residence time of about 5 seconds to about one minute.

20. A method of claim 18,
wherein said second reaction fluid has a temperature of about 358° C. to about 380° C. at a pressure of about 200 bar to about 260 bar.

21. A method of claim 18,
wherein said slurry is contacted with said second reaction fluid for less than about 5 seconds.

22. A method of claim 18,
wherein, prior to said reducing the temperature step, said second reaction mixture is cooled to a temperature of about 260° C. to about 280° C. at a pressure of about 200bar to about 260 bar.

23. A method of claim 18, further comprising:
fractionating said lignocellulosic biomass prior to said providing step;
wherein said step of fractionating comprises contacting said lignocellulosic biomass with a first reaction fluid comprising hot compressed water and, optionally, carbon dioxide;
wherein said first reaction fluid further comprises acid, when said lignocellulosic biomass comprises softwood; and
wherein said first reaction fluid is at a temperature of at least about 100° C. under a pressure sufficient to maintain said first reaction fluid in liquid form.

24. A method of claim 18,
wherein said method is continuous.

25. A method of claim 18,
wherein said reducing the temperature of said second reaction mixture comprises contacting said second reaction mixture with a composition comprising water.

26. A method of claim 25,
wherein said composition further comprises at least one $C_1$-$C_5$ alcohol.

27. A method of claim 18,
wherein said reducing the temperature of said second reaction mixture comprises contacting said second reaction mixture with a composition comprising water and acid, wherein said acid is present at a level less than about 1%, by weight, based on the total weight of said composition.

28. A method of claim 27,
wherein said composition further comprises at least one $C_1$-$C_5$ alcohol.

29. A method of claim 18,
wherein said hydrolyzing said second liquid fraction is carried enzymatically.

30. A method of claim 18,
wherein said hydrolyzing said second liquid fraction is carried with immobilized enzyme.

31. A method of claim 18,
wherein said hydrolyzing said second liquid fraction comprises addition of at least one aqueous acid.

32. A method of claim 18,
wherein said hydrolyzing said second liquid fraction comprises contact with a gaseous compound that forms acid in situ.

33. A method of claim 18,
wherein said hydrolyzing said second liquid fraction comprises contact with at least one solid acid catalyst.

34. A method of claim 18,
wherein the yield of said glucose is at least about 63% of theoretical yield.

35. A method of reducing the rate of glucose degradation, comprising:
providing lignocellulosic biomass, comprising:
a first solid fraction comprising:
cellulose; and
lignin; and
a first liquid fraction;
optionally, separating said first solid fraction and said first liquid fraction;
mixing said first solid fraction with water to form a slurry;
pre-heating said slurry to a temperature of about 210° C. to about 240° C. at a pressure of about 225 bar to about 250 bar;
contacting said slurry with a second reaction fluid to form a second reaction mixture comprising:
a second solid fraction comprising:
lignin; and
a second liquid fraction comprising:
a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C. under a pressure sufficient to maintain said second reaction fluid in supercritical form; and
reducing the temperature of said second reaction mixture to a temperature less than about 140° C.; and
optionally, hydrolyzing said second liquid fraction to form a composition comprising at least one $C_6$ saccharide selected from the group consisting of $C_6$ oligosaccharide having lower mer units, glucose, galactose, mannose, fructose, and mixtures thereof.

36. A method of claim 35, further comprising:
preheating said slurry to a temperature of about 245° C. to about 255° C. at a pressure of about 200 bar to about 260 bar for a residence time of about 5 seconds to about one minute.

37. A method of claim 35,
wherein said second reaction mixture has a temperature of about 358° C. to about 380° C. at a pressure of about 200 bar to about 260 bar.

38. A method of claim 35,
wherein said slurry is contacted with said second reaction fluid for less than about 5 seconds.

39. A method of claim 35,
wherein, prior to said reducing the temperature step, said second reaction mixture is cooled to a temperature of about 260° C. to about 280° C. at a pressure of about 200 bar to about 260 bar.

40. A method of claim 35,
wherein said fractionating comprises contacting said lignocellulosic biomass with a first reaction fluid comprising hot compressed water and, optionally, carbon dioxide;
wherein said first reaction fluid further comprises acid, when said lignocellulosic biomass comprises softwood; and
wherein said first reaction fluid is at a temperature of at least about 100° C. under a pressure sufficient to maintain said first reaction fluid in liquid form.

41. A method of claim 35,
wherein said method is continuous.

42. A method of claim 35,
wherein said reducing the temperature of said second reaction mixture comprises contacting said second reaction mixture with a composition comprising water.

43. A method of claim 42,
wherein said composition further comprises at least one $C_1$-$C_5$ alcohol.

44. A method of claim 35,
wherein said reducing the temperature of said second reaction mixture comprises contacting said second reaction mixture with a composition comprising water and acid, wherein said acid is present at a level less than about 1%, by weight, based on the total weight of said composition.

45. A method of claim 44,
wherein said composition further comprises at least one $C_1$-$C_5$ alcohol.

46. A method of claim 35,
wherein said hydrolyzing said second liquid fraction is carried enzymatically.

47. A method of claim 35,
wherein said hydrolyzing said second liquid fraction is carried with immobilized enzyme.

48. A method of claim 35,
wherein said hydrolyzing said second liquid fraction comprises addition of at least one aqueous acid.

49. A method of claim 35,
wherein said hydrolyzing said second liquid fraction comprises contact with a gaseous compound that forms acid in situ.

50. A method of claim 35,
wherein said hydrolyzing said second liquid fraction comprises contact with at least one solid acid catalyst.

51. A method of claim 35,
wherein the yield of said glucose is at least about 63% of theoretical yield.

52. A method, comprising:
providing lignocellulosic biomass, comprising:
a first solid fraction comprising:
cellulose; and
lignin; and
a first liquid fraction;
optionally, separating said first solid fraction and said first liquid fraction;
mixing said first solid fraction with water to form a slurry;
pre-heating said slurry to a temperature of about 210° C. to about 240° C. at a pressure of about 225 bar to about 250 bar;

contacting said slurry with a second reaction fluid to form a second reaction mixture comprising:
   a second solid fraction comprising:
      lignin; and
   a second liquid fraction comprising:
      a soluble $C_6$ saccharide selected from the group consisting of $C_6$ monosaccharides, $C_6$ oligosaccharides, and mixtures thereof;
wherein said second reaction fluid comprises hot compressed water and, optionally, carbon dioxide;
wherein said second reaction fluid is at a temperature of at least about 373° C. under a pressure sufficient to maintain said second reaction fluid in liquid form; and
reducing the temperature of said second reaction mixture to a temperature less than about 140° C.; and
hydrolyzing said second liquid fraction to form a composition comprising at least one $C_6$ saccharide selected from the group consisting of $C_6$ oligosaccharide having lower mer units, glucose, galactose, mannose, fructose, and mixtures thereof; and
converting by fermentation, catalysis, or a combination thereof said $C_6$ saccharides to a fermentation product, a catalysis product, or a mixture thereof.

* * * * *